United States Patent
Morris et al.

(10) Patent No.: US 7,164,123 B2
(45) Date of Patent: Jan. 16, 2007

(54) METHOD FOR FILTERING SPURIOUS RESONANCES FROM AN NMR DATASET

(75) Inventors: Peter G. Morris, Nottingham (GB); Terry Moore, Ely (GB); Paul Anuzis, Derby (GB); Kenneth Astley, Derby (GB)

(73) Assignee: Rolls-Royce plc, London (GB)

( * ) Notice: Subject to any disclaimer, the term of this patent is extended or adjusted under 35 U.S.C. 154(b) by 0 days.

(21) Appl. No.: 11/318,543

(22) Filed: Dec. 28, 2005

(65) Prior Publication Data

US 2006/0164085 A1 Jul. 27, 2006

Related U.S. Application Data

(63) Continuation of application No. PCT/GB04/02616, filed on Jun. 17, 2004.

(30) Foreign Application Priority Data

Jul. 14, 2003 (GB) .................... 0316440.7

(51) Int. Cl.
*G01V 3/00* (2006.01)
(52) U.S. Cl. ............... 250/287; 324/307; 324/306; 324/333; 324/336; 73/151
(58) Field of Classification Search .............. None
See application file for complete search history.

(56) References Cited

U.S. PATENT DOCUMENTS 4,656,425 A 4/1987 Bendel
4,710,713 A 12/1987 Strikman
6,956,370 B1 * 10/2005 Heidler ................. 324/303

FOREIGN PATENT DOCUMENTS

| EP | 0 967 490 | 12/1999 |
| EP | 1 191 330 | 3/2002 |
| EP | 1 063 535 | 7/2003 |
| JP | 2 255 127 | 10/1990 |

OTHER PUBLICATIONS

I.P. Gerothanassis; Methods of Avoiding the Effects of Acoustic Ringing in Pulsed Fourier Transform Nuclear Magnetic Resonance Spectroscopy; Pergamon Press, 1987.
Fukushima; Experimental Pulse NMR—A Nuts and Bolts Approach; Experimental Pulse NRM; 1981.

* cited by examiner

*Primary Examiner*—Nikita Wells
*Assistant Examiner*—Zia R. Hashmi
(74) *Attorney, Agent, or Firm*—W. Warren Taltavull; Manelli Denison & Selter PLLC (57) ABSTRACT

A method for filtering spurious resonances from an NMR dataset comprises the steps of:
(a) creating a first, non-oscillating magnetic field of a predetermined field strength across a sample,
(b) intermittently exposing the sample to a second, oscillating magnetic field orthogonal to the first to generate an NMR signal,
(c) detecting the NMR signal from the sample,
(d) adjusting the first magnetic field to a different predetermined field strength and repeating steps (a) to (c), and
(d) comparing the detected signals to obtain an NMR dataset from the sample from which spurious resonances have been filtered.

22 Claims, 7 Drawing Sheets

Fig. 1a.

there is a magnetic

METHOD FOR FILTERING SPURIOUS RESONANCES FROM AN NMR DATASET

This is a continuation of International Application No. designating the U.S. PCT/GB2004/002616 filed Jun. 17, 2004.

FIELD OF THE INVENTION

This invention is generally concerned with a method for filtering spurious resonances from a Nuclear Magnetic Resonance (NMR) dataset. In particular, although not necessarily exclusively, the NMR dataset may derive from a sample from a fluid system. Example fluid systems are, the flow of oil (e.g. engine lubricating or cooling oil), fuel, coolants (e.g. water) or hydraulic fluid in a power plant or other machinery.

BACKGROUND

Liquids such as oils, fuels and hydraulic fluids are very frequently used in environments in which they are liable to become contaminated, typically with particulate matter. Taking engine lubricating oils as an example, engine components over which the oil washes are subject to wear, creating small particles, often referred, to as "chips" or "fines", which are entrained in the oil flow.

These particles, and other particulate debris, may indicate engine component wear and are factors in the deterioration of the condition of the oil and may also cause damage to other engine components if allowed to freely circulate with the lubricating oil flow. In-line collectors, such as filters and gauzes, are therefore used to collect the debris, the collectors being checked and emptied on a regular basis.

Collection and analysis of the particulate debris can also provide information about the condition of oil washed components of the engine. For example, an excessive amount of debris can indicate excessive wear of a component and thereby highlight a potential problem. By analysing the debris, in particular its composition, it is also possible to narrow down the number of components from which the debris might originate, making the task of identifying the faulty or problem component an easier one. In some cases debris may be indicative of a precursor to failure. For example, if bearing cage coating material is identified indicating that the cage is damaged, it will be some time before a bearing is likely to fail due to this damage.

However, the regular checking and emptying of the collectors, and the analysis of the collected debris, amount to a burdensome manual maintenance requirement that it would be desirable to avoid. Moreover, the checking and emptying of the collectors are intrusive processes, which must necessarily be undertaken when the engine is not operating.

In addition to the problems associated with contaminants, particulate or otherwise, liquids such as those discussed above, which often work in very harsh environments, tend to experience a gradual deterioration over time. This deterioration may be of the base liquid itself, for example a change in structure or composition, and/or a loss or reduction in the efficacy of intentional additives (liquid or particulate) to the liquid, for example rust inhibitors or friction reducing additives in oil, which breakdown over time. As with the detection of contaminants, the task of monitoring this deterioration, by sampling and analysing the oil or other liquid, is intrusive and time consuming.

EP 1191330 describes NMR techniques for the detection and analysis of anomalies in fluid systems. However, before discussing these techniques further, it is useful to give a brief overview of the relevant NMR theory.

Certain atomic nuclei possess angular momentum and the quantum property of "spin". Because the nuclei also carry a charge, specifically a positive charge, there is a magnetic moment associated with this spin. When placed in a magnetic field, these nuclei, which might be referred to as the nuclear "magnets", tend to align with the field direction. Only certain orientations are possible—two in the case of a spin ½ nucleus such as a proton.

The energy difference between the orientations of the nuclei ("Zeeman splitting") depends linearly on the strength of the magnetic field B. Transitions between the two orientations can be induced when the frequency of an applied oscillating magnetic field (normally electromagnetic radiation such as a radio frequency (RF) signal), exactly matches the energy difference. This so called resonance condition, is defined by the Larmor equation:

$$\omega = \gamma B$$

where $\omega$ is the angular frequency of the oscillating magnetic field (electromagnetic radiation) and $\gamma$, referred to as the magnetogyric ratio, is a constant for a particular nuclear species.

Different nuclei have different values of $\gamma$ and so resonate at different frequencies in a magnetic field of given strength. For example, at 11.7 T, resonant frequencies for the following nuclei are: $^1$H—500 MHz; $^{13}$C—125.7 MHz; $^{27}$Al—130.3 MHz; $^{29}$Si—99.3 MHz; $^{51}$V—131.5 MHz; $^{53}$Cr—28.3 MHz; $^{55}$Mn—123.3 MHz; $^{59}$Co—118.1 MHz, $^{95}$Mo—32.6 MHz; $^{107}$Ag—23.3 MHz and $^{183}$W—20.8 MHz.

The magnetic field B in the Larmor equation given above is the actual field strength at the nucleus and includes susceptibility effects arising from the bulk magnetic properties of the sample, local variations in these effects due to sample heterogeneity, and the screening effect of the electrons that surround the nucleus itself. Thus:

$$B = B_0(1+\chi)$$

where $\chi$ is the magnetic susceptibility and $B_0$ is the applied magnetic field.

In traditional high resolution NMR, it is the contribution of the screening electrons to $\chi$ that gives the technique its power to analyse chemical structure: the same nucleus (e.g. $^1$H) will experience different magnetic fields depending on the chemical environment, so that chemically distinct nuclei resonate at slightly different frequencies. The range of these chemical shifts for any particular nucleus is, however, small: 0–10 ppm covers most $^1$H resonances of interest. In order to resolve them, the main applied magnetic field $B_0$ must be maintained homogeneous over the sample volume. A few parts in $10^9$ are commonplace and a few parts in $10^{10}$ achievable with spinning samples under ideal conditions.

However, the general premise on which the NMR techniques of EP 1191330 are based is that the NMR characteristics of a fluid system can be influenced by anomalies in the fluid system.

In particular, EP 1191330 proposes that such anomalies can be detected and analysed in two ways. The first way is termed "indirect detection" and involves analysing the influence the anomalies have on a signal from the fluid rather than analysing a signal from the anomalies themselves. This is particularly useful for the detection of inhomogeneities, such as particulates, in the fluid. The approach is possible where the particulates have a different magnetic susceptibility than the fluid, because they will then cause local non-uniformities in the magnetic field. This in turn modifies the NMR signal from the fluid, manifesting itself, for instance, in changes of line-width and/or position of the fluid resonance seen in the NMR frequency domain.

The second way is termed "direct detection" and, to the extent that the NMR signal that is detected and analysed does derive directly from a contaminant or additive in the fluid system, it is closer to traditional NMR techniques.

Direct detection can be used to detect inhomogeneities or dissolved species in the fluid.

According to EP 1191330, the above detection techniques can be performed using pulsed or continuous wave (CW) NMR spectroscopy.

Historically, CW NMR spectroscopy was the first to be developed (see e.g. N. Bloembergen, "Nuclear Magnetic Relaxation", W. A. Benjamin, Inc., N.Y., 1961 and, E. R. Andrew, "Nuclear Magnetic Resonance", Cambridge University Press, Cambridge, 1955). In CW NMR, a first, non-oscillating magnetic field of a predetermined field strength is created across a sample, which is also exposed to a second, oscillating magnetic field orthogonal to the first. The frequency of the oscillating magnetic field or the strength of the non-oscillating magnetic field is varied to sweep through the resonance condition and generate an NMR signal. For example, Bloembergen and Andrew both describe experimental arrangements in which a permanent magnet produces a "steady" non-oscillating magnetic field across the sample, and adjacent coils vary the strength of this steady field.

Modern NMR machines, however, mostly use pulsed NMR spectroscopy. These involve creating a first, non-oscillating magnetic field of a predetermined field strength across the sample, and intermittently exposing the sample to a second, oscillating magnetic field orthogonal to the first to generate an NMR signal. The relatively short pulse width (typically of the order of µs) of the intermittent field makes it possible to simultaneously detect a range of frequencies in the NMR signal. A significant advantage of pulsed NMR over CW NMR is that much greater signal-to-noise ratios can be achieved. Essentially, this is because the time between each pulse of the intermittent field is much shorter than each CW sweep through the resonance condition so that in a given period more useful information can be obtained with pulsed NMR than CW NMR (for a more detailed explanation see e.g. A. E. Derome, "Modern NMR Techniques for Chemistry Research", Pergamon Press, 1987).

The trend in modern NMR spectroscopy is towards pulsed NMR with high non-oscillating field strengths and high resolutions. Largely this has been made possible by developments in the technology of superconducting magnets. It is difficult to modulate the magnitude of the field of such magnets, but so-called shim coils are used to locally increase the homogeneity of the field in the region of the sample under study. Most of these do so by producing magnetic fields varying in strength with distance from the magnetic centre (normally according to spherical harmonic distributions). However, the $B_0$ shim coil produces a zeroth order, uniform field along the direction of the main $B_0$ field that adds or subtracts from the main $B_0$ field.

In contrast the NMR techniques described in EP 1191330 are suitable for performance at relatively low non-oscillating field strengths (e.g. 1.5 T or less). However, particularly at low non-oscillating field strengths (i.e. low resonant frequencies), a problem associated with the performance of NMR spectroscopy is that spurious resonances arising from the electrical or mechanical components of the NMR apparatus can interfere with the sample resonances, even to the extent of exceeding or swamping the sample resonances. Thus the spurious resonances can lead to low signal-to-noise-ratios.

SUMMARY OF THE INVENTION

An insight of the present inventors was that many spurious resonances are relatively insensitive to the strength of the non-oscillating field, so that repetition of an NMR experiment at different non-oscillating field strengths allows the spurious resonances to be identified and hence reduced or removed.

Accordingly a first aspect of the invention provides a method for filtering spurious resonances from an NMR dataset, comprising the steps of:
  (a) creating a first, non-oscillating magnetic field of a predetermined field strength across a sample,
  (b) intermittently exposing the sample to a second, oscillating magnetic field orthogonal to the first to generate an NMR signal,
  (c) detecting the NMR signal from the sample,
  (d) adjusting the first magnetic field to a different predetermined field strength and repeating steps (a) to (c), and
  (d) comparing the detected signals to obtain an NMR dataset from the sample from which spurious resonances have been filtered.

And a second aspect of the invention provides a method for filtering spurious resonances from an NMR dataset, comprising the steps of:
  (a) creating a first, non-oscillating magnetic field of a predetermined field strength across a sample,
  (b) exposing the sample to a second, oscillating magnetic field orthogonal to the first,
  (c) continuously varying (typically in a linear fashion) the field strength of the non-oscillating field and/or the frequency of the oscillating field to generate an NMR signal,
  (d) detecting the NMR signal from the sample,
  (e) adjusting the first magnetic field to a different predetermined field strength and repeating steps (a) to (d), and
  (f) comparing the detected signals to obtain an NMR dataset from the sample from which spurious resonances have been filtered.

The first aspect relates to pulsed NMR and the second to CW NMR. Pulsed NMR is preferred.

Typically, the field strength of the first magnetic field is adjusted by less than 0.5% and more typically by 0.35% or less. However, preferably, the field strength of the first magnetic field is adjusted by at least 0.15%. In general, the amount of adjustment will depend on e.g. the strength of the first magnetic field and the chemical shift range of the nucleus under study.

Preferably, the first, non-oscillating, magnetic field is uniform across the sample. That is, it does not expose the sample to substantial magnetic field gradients.

Preferably, the filtered dataset is transformed into an NMR frequency domain spectrum, for example using well known Fourier transform techniques. Optionally, the detected signals can be transformed in this way before they are compared. However, in the case of pulsed NMR, the detected signals can be compared in the form of free induction decays, and the filtered dataset can take this form too.

Sample resonance(s) are sensitive to the value of the field strength in the region of the sample under study, whereas spurious resonances from the components of the NMR apparatus are relatively insensitive to it. Thus during the comparison step, the spurious resonances can be identified as they persist independent of field strength. In contrast, sample resonances move with the field according to the Larmor equation. The ability to identify spurious resonances in this way allows them to be filtered from the NMR dataset.

Conventionally, NMR is carried out using high magnetic field strengths, often of the order of 5–20 T or more, corresponding to high resonant frequencies (RF signals), in the order of 200–900 MHz for $^1$H, to produce high resolution spectra. However, in preferred implementations, the present invention proposes to use relatively low field strengths and frequencies, preferably field strengths no higher than 1.5 T, more preferably 1 T or less and even. more preferably 0.5 T or less, corresponding respectively to $^1$H resonant frequencies of about 64 MHz, 43 MHz and 21 MHz. In fact, $^1$H resonant frequencies as low as 1 MHz, i.e. magnetic field strengths as low as 0.0235 T, are not impractical, and even lower field strengths than this may provide useful results.

This preferred approach gives a low resolution output, the effect of which is that the series of peaks seen in a high resolution frequency spectrum merge to form a single peak or resonance.

It may be thought that this loss of resolution would be disadvantageous, because a degree of information is lost from the NMR signal. However, as explained in EP 1191330, it has been found that the presence of inhomogeneities in fluid systems such as particulates or immiscible fluid droplets, can nevertheless be reliably detected, and this low resolution approach has the significant advantage that subsequent analysis is greatly simplified. The possibility it provides for using much less powerful, and hence much smaller magnets than conventional techniques is also a significant advantage.

In preferred embodiments, the sample is a fluid sample from a fluid system. Such a system may be a mixture of more than one liquid, mixtures of more than one gas, and mixtures of liquids and gases.

The invention can be used in the performance of the "indirect" and "direct" detection methods of EP 1191330. Thus it has particular application in the detection of particulate or immiscible fluid contaminants or additives in a flowing liquid, for example a flow of oil (e.g. engine lubricating or cooling oil), fuel, coolants (e.g. water) or hydraulic fluid in a power plant or other machinery, and in the detection of dissolved species (whether present as contaminants or additives) in such a liquid. Such detection typically relates to the monitoring, preferably in situ, of the health of a fluid system.

For example, to "indirectly" detect the presence of an inhomogeneity in a sample from a fluid system, at least one of the generated NMR signals should include a fluid resonance. The method then also comprises a step of analysing the filtered dataset to look for changes caused by a variation of the width and/or position of the fluid resonance in the NMR spectrum for the sample, the variation being indicative of the presence of the inhomogeneity.

Usually indirect detection techniques will involve looking at the $^1$H resonance of the fluid system, since hydrogen is a common element in many fluids, including for example oils, fuels, water etc. In general, the $^1$H resonance is relatively strong compared to spurious resonances, so that the method of the present invention may provide only marginal benefits in relation to improved signal-to-noise ratios.

Greater benefits are generally seen in relation to "direct" detection techniques, where the resonances of interest are often substantially weaker than the $^1$H resonance. Direct detection can be used to identify the presence and elemental composition of inhomogeneities (particulates or fluid droplets) or dissolved species in a sample from a fluid system. In direct detection, for one or more of the generated NMR signals, the predetermined field strength of the non-oscillating field and/or the frequency of the oscillating field is selected in accordance with the magnetogyric ratio of the inhomogeneity or dissolved species to be detected. The method also comprises a step of analysing the filtered dataset to look for changes in said one or more signals indicative of the presence of the inhomogeneity or dissolved species in the fluid.

The direct approach has many applications, including for example monitoring the level of additives or contaminants in oil or fuel, e.g. water contamination of fuel.

The direct approach can be repeated a plurality of times, at each repetition the predetermined field strength of the non-oscillating field and/or the frequency of the oscillating field being selected to correspond to a different magnetogyric ratio. In this way, a sequential, non-intrusive analysis of the composition of contaminants, additives or other NMR-detectable material in a fluid system can be conducted. The NMR signals, typically transformed into frequency spectra, detected with this direct method can be empirically related to amounts, i.e. concentrations of the nuclear species in the fluid system. This is because the NMR signal intensity is proportional to the number of nuclei present in the sample.

However, at low non-oscillating field strengths, it is also possible to select the predetermined field strength of the non-oscillating field and/or the frequency of the oscillating field such that two or more species are identifiable in the filtered dataset. This is possible because the effect of low field strengths is to bring the resonant frequencies of different atomic species closer together. Of course, conventionally low field strengths have implied low signal-to-noise ratios, but by adopting the filtering approach of the present invention, useful signal-to-noise ratios can be achieved.

Preferably a $B_0$ shim coil or coils is provided to adjust the first magnetic field to each different predetermined field strength. For example, a current can be passed through the coil(s) to produce a $B_0$ shim field which strengthens or weakens the non-oscillating magnetic field by a desired amount at each repetition of steps (a) to (c) of the pulsed NMR method or steps (a) to (d) of the CW NMR method.

As noted above in the discussion of the underlying NMR theory, different nuclear species can be characterised by different magnetogyric ratios (γ) and so resonate at different frequencies of the oscillating magnetic field for a given field strength of the non-oscillating field. By changing the field strength of the non-oscillating field it is possible to focus detection on specific nuclear species or to include several species in a single spectrum. The $B_0$ shim coil(s) can be used to accomplish this change of field strength, and thus can be used to focus detection as well as to filter spurious resonances.

Furthermore, in direct detection, sequential analysis of each of a plurality of nuclear species with different magnetogyric ratios can be performed, e.g. by using the $B_0$ shim coil(s) to change the field strength of the non-oscillating field such that detection is focused on each of the species in turn. Alternatively, if the intention is to identify more than one species in the same filtered dataset, the $B_0$ shim coil(s)

can be used to position the field strength of the non-oscillating field such that simultaneous detection of each species is possible.

Whether employing a single- or multi-nuclei approach, it may be possible to use this approach to provide useful information about the source of a contaminant in a fluid system. For instance, taking the example of engine oil, the composition of the debris entrained in the oil may give an indication of the engine component from which the debris has come, indicating wear of that component. This use of the method to detect the source of a contaminant can be enhanced by including one or more marker nuclei in potential contaminant sources which are released into the fluid system as part of the contaminant. For instance, taking the engine oil example once more, it might be desirable to dope critical engine components with nuclei which can be easily detected in the oil so that their wear can be readily monitored. Elements that might be selected for sequential detection in an oil stream associated with a mechanical equipment include silver, manganese, aluminium, vanadium and cobalt.

In relation to the direct approach as applied to particulates, it may be useful to entrap the particles adjacent the NMR detector in a system (e.g. an oil filter) which would otherwise carry them away with a flow of the fluid system. This has the advantage of increasing the local concentration of the particulates over time, with a resultant strengthening of the NMR signal.

Whilst it is possible for any of the above described techniques to be applied to a stationary liquid sample, one significant advantage of this non-intrusive approach is that the "sample" can simply be an element of a liquid flow, for example flowing through a conduit extending through the generated magnetic fields. This possibility for in situ, non-intrusive detection and analysis of contaminants can remove the need for regular sampling and checking of the fluid system, for example the regular checking of filters or other debris collectors.

In the various aspects discussed above, the oscillating magnetic field may be provided by a further coil carrying an alternating current, driven to produce an RF (radio frequency) signal, the magnetic component of which provides the desired field. Conveniently, the same coil may be used to detect the NMR signal.

In further aspects, the invention also provides systems, operable in accordance with any one of the methods discussed above, for filtering spurious resonances from an NMR dataset.

For performing pulsed NMR, a typical system comprises a sample holder (which may be a filter or a conduit through which a fluid flows, and which may be metallic if it contains the transceiver coil); means for generating a first, non-oscillating magnetic field across the holder; means for adjusting the field strength of the first magnetic field; means for simultaneously generating a second, intermittent oscillating magnetic field across the holder; means for detecting resulting NMR signals from within the holder; and processing means operable in accordance with the first aspect of the invention discussed above for comparing the detected signals to obtain an NMR dataset from the sample from which spurious resonances have been filtered.

For performing CW NMR, a typical system comprises a non-magnetic, sample holder (which may be a filter or a conduit through which a fluid flows, and which may be metallic if it contains the transceiver coil); means for generating a first, non-oscillating magnetic field across the holder; means for adjusting the field strength of the first magnetic field; means for simultaneously generating a second, oscillating magnetic field across the holder; means for continuously varying the field strength of the non-oscillating field and/or the frequency of the oscillating field; means for detecting resulting NMR signals from within the holder; and processing means operable in accordance with the second aspect of the invention discussed above for comparing the detected signals to obtain an NMR dataset from the sample from which spurious resonances have been filtered.

The processing means may further transform the filtered dataset into an NMR frequency domain spectrum. Alternatively, the processing means may transform the detected signals into NMR frequency domain spectra before they are compared.

The processing means may have further capability to perform the direct and/or indirect detection techniques described above.

The means for adjusting the field strength of the first magnetic field may be a coil, and preferably a $B_0$ shim coil or coils for producing a $B_0$ shim field. In the CW NMR system, such a coil or coils may also perform the function of continuously varying the field strength of the non-oscillating field.

The oscillating magnetic field generating means and the NMR signal detecting means may each comprise a further coil surrounding the conduit, for example an RF-coil. Preferably, a single coil performs both functions.

In one exemplary application, the sample holder may be a debris collector, such as a filter.

BRIEF DESCRIPTION OF THE DRAWINGS

The invention will be described by way of example with reference to the accompanying drawings, in which:

FIGS. 4a, b and c show NMR spectra for an aqueous solution of potassium permanganate and aluminium nitrate.

DETAILED DESCRIPTION OF EMBODIMENTS AND EXAMPLES

Figure 1A:
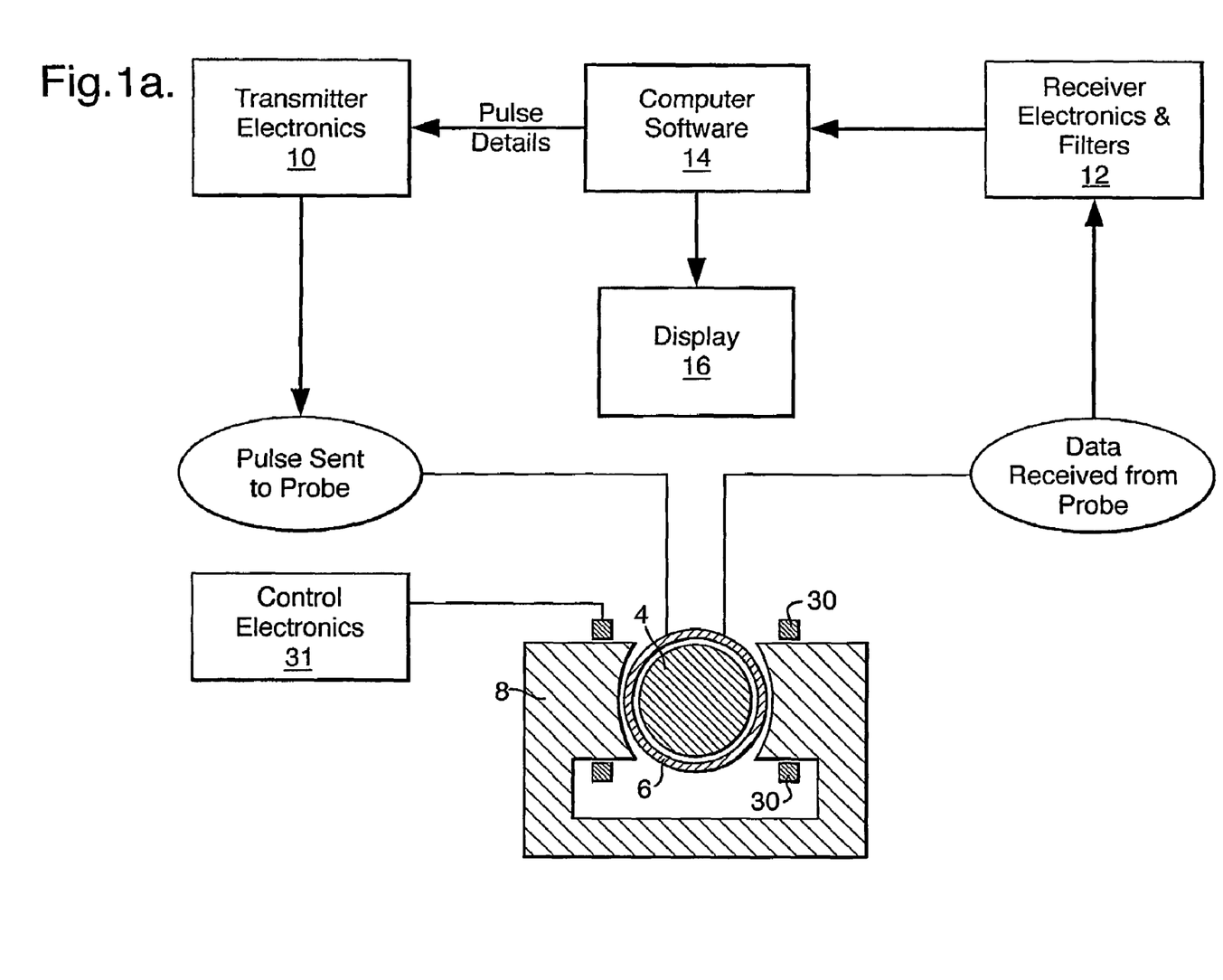
FIGS. 1a and b show schematically an apparatus for detecting inhomogeneities or dissolved species in a liquid flow.
Figure 1B:
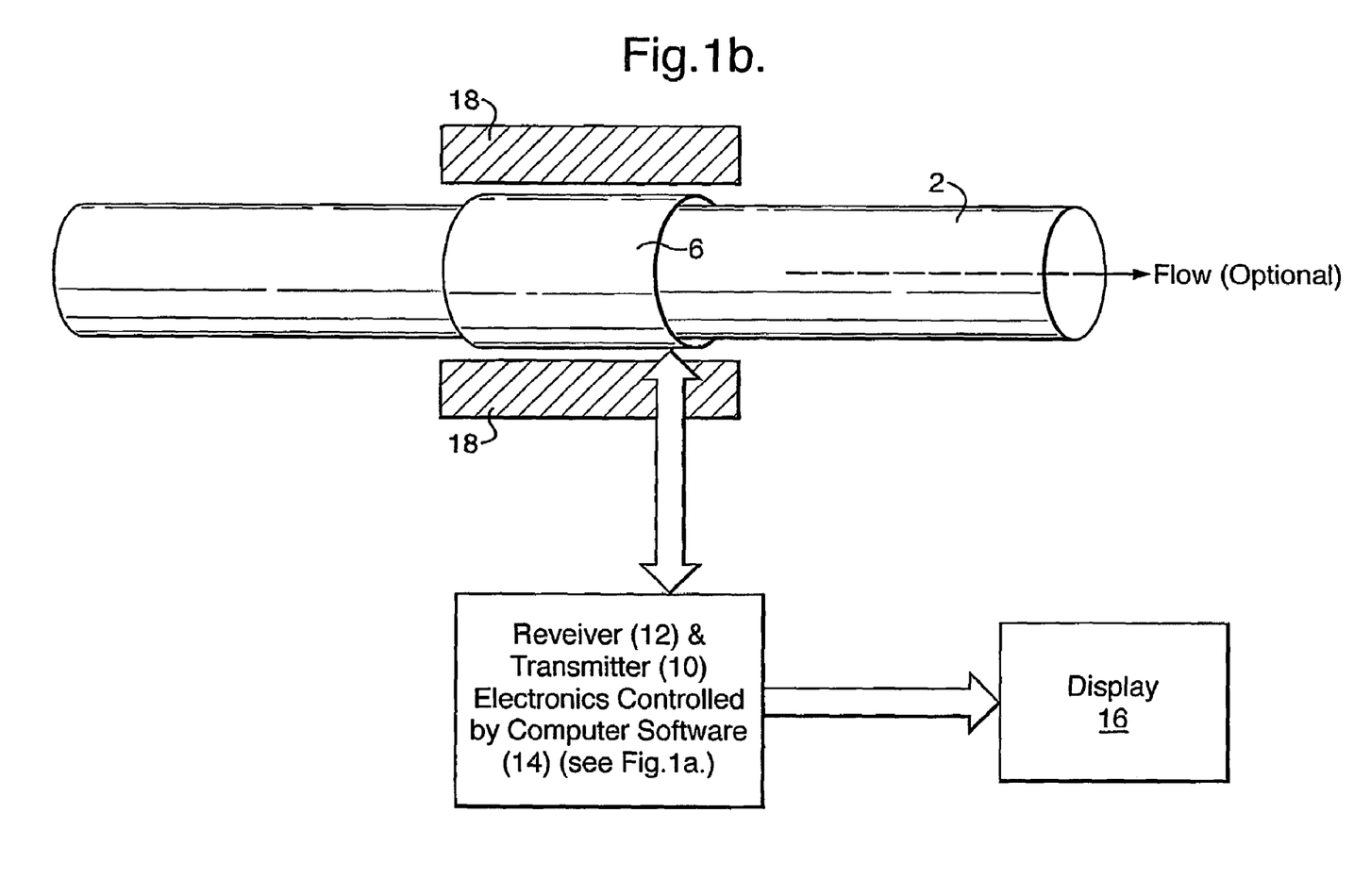

Methods according to various aspects of the invention will be exemplified by way of a test which has been implemented using a 2.278 MHz bench-top NMR spectrometer suitable for the study of suspended debris (e.g. in engine oil) or the composition of solutions. The system is illustrated schematically in FIGS. 1 and 2.

Figure 2:
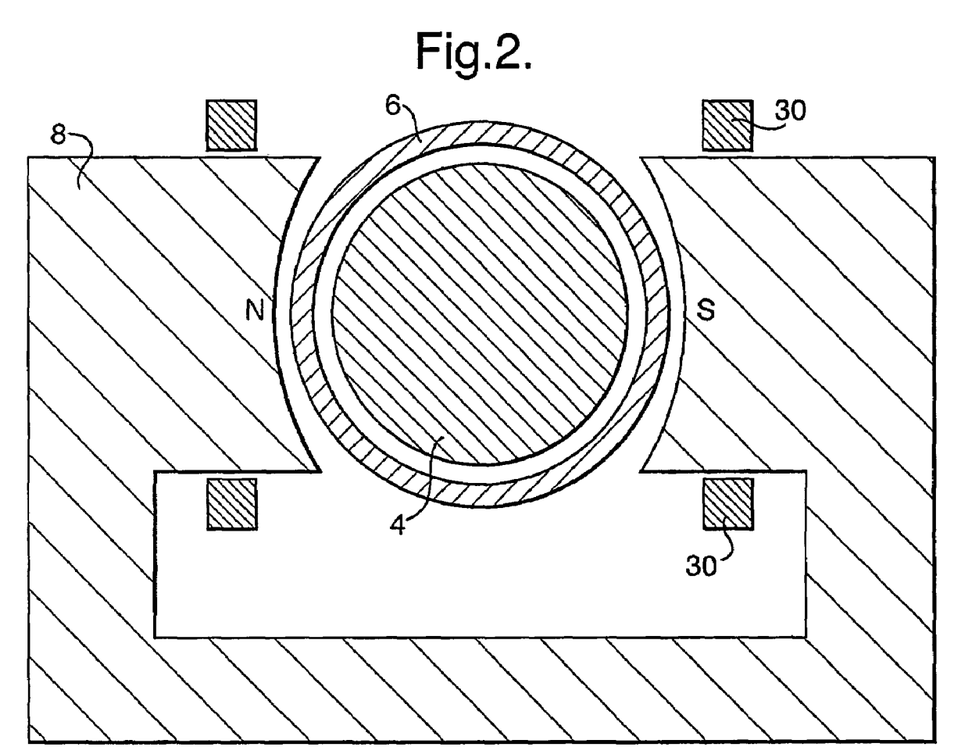
FIG. 2 shows schematically a cross-section through the magnet and coil arrangement of the apparatus of FIGS. 1a and b.

Looking at the system as a whole, the main components are a non-ferromagnetic sample pipe 2, within which a liquid sample to be evaluated flows or a static sample can be placed, an annular probe head 6 that surrounds the sample pipe 2, and hence the sample 4 itself, a magnet 8 which partially surrounds the probe head 6, and current-carrying $B_0$ shim coils 30.

The magnet 8 provides a fixed strength, non-oscillating magnetic field, and $B_0$ shim coils 30 are arranged to produce a $B_0$ shim field which is parallel to and superimposed upon this non-oscillating field. The $B_0$ shim field is in the same or opposite direction to the main static field generated by magnet 8. A simple and accurate way of driving the $B_0$ shim field is to provide a Helmholtz pair of $B_0$ shim coils (as shown in FIGS. 1*a* and 2), but with more coils or distributed windings, better homogeneity can be achieved. The probe head 6 both generates an oscillating magnetic field to excite the sample and serves as a detector for the resulting NMR signals from the sample.

The probe head is driven to generate its oscillating magnetic field in a pulse mode by conventional transmitter electronics 10. Further conventional control electronics 31 is configured to control the current to the $B_0$ shim coils 30 and hence the strength of the $B_0$ shim field. The control electronics should deliver a stable current (and hence field) and can be under control of computer software 14.

NMR signals detected by the probe 6 are collected by conventional receiver electronics 12. The transmitter and receiver electronics are controlled by a digital computer under the instruction of appropriate software 14. The software processes the received NMR signals (e.g. to produce frequency domain spectra) and can display the signals or processed signals on an associated display 16.

Figure 3:
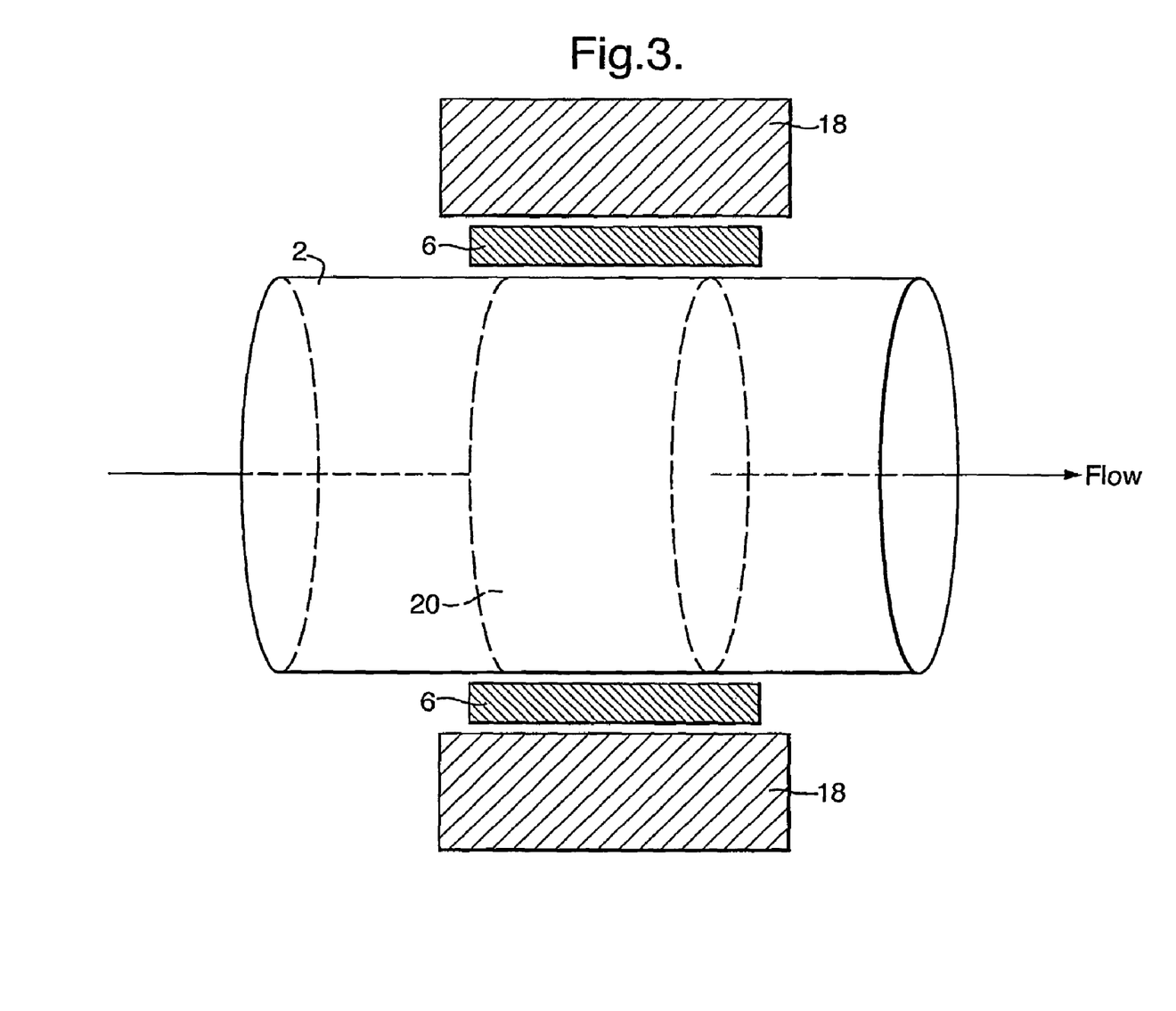
FIG. 3 schematically shows a debris trap in an oil pipe.

As illustrated schematically in FIG. 3, a particle filter assembly 20 may be located in the pipe adjacent the probe head 6, in order to accumulate particulate material, making the study of its build up over time easier. The particle filter can also provide the function of a standard particle trap conventionally used in e.g. circulating oil systems. However, rather than having to periodically dismantle the system to check and empty the filter, the system can provoke an operator to check the filter contents based on a detected fault initiation.

The magnet 8 used in this exemplary bench-top system is a horseshoe-shaped magnet made from light weight, high temperature stable, bonded alloy. Other forms of magnet, including electromagnets may be used. An example of a particularly appropriate magnet, which is very compact and light weight, is described in U.S. Pat. No. 5,635,889.

The magnetic field generated by the horseshoe magnet 8 of the present example is 0.256 T. The polepiece 18 diameter is 125 mm with a 56 mm gap between the pole faces.

The probe head 6 includes a combined RF transmitter and receiver coil to perform both the magnetic field generation and NMR signal detection functions. The probe coil is solenoidal, of length 50 mm, wound on a PTFE body, and can take a sample pipe of up to 26 mm in diameter.

Used with the system described above, the probe 6, operating at 25 W, has a point of maximum sensitivity which is tunable between about 0.653 and 0.688 MHz (i.e. 0.6705 MHz±2.54%). To an extent, this allows it to be tuned to a particular resonance of interest, i.e. characteristic of the specific nuclear species (e.g. elemental isotope) to be observed. However, other probe coils are available which can be switched in the system. For example, we have also tested probe coils centred at about 2.8 MHz and 0.182 MHz.

However, in the present study, adjustment of the strength of the $B_0$ shim field to match the resonant frequency of the nuclei of interest to the frequency of the probe 6 could be used to supplement or replace tuning of the probe. This adjustment was achieved by varying the current through $B_0$ shim coils 30.

The magnet 8, $B_0$ shim coils 30, and probe head 6 are contained in a programmable temperature controlled enclosure (not shown). Further enclosures hold the associated electronics 10, 12, 31.

When the coil within the probe 6 is in resonance with the precessing nuclei of interest, data can be obtained in response to the type of pulse programme used. The computer both stores the pulse programme and controls the timings and way it is run. All the pulse programmes used in the tests are conventional.

A simple pulse-acquire pulse sequence has been found sufficient to detect the presence of a compound through one of its constituent elements, although other pulse sequences may be used. The programme is run when the sample is present and the variables in the programme optimised to give the largest signal. The pulse of radio-frequencies from the probe 6 nutates the nuclear magnetisation away from the static field direction, whereupon it precesses about the magnetic field at the Larmor frequency, and is detected by the receiver. The signal gradually decays, often in an approximately exponential manner. This is known as a free induction decay or FID. This AC signal is digitised by an analogue to digital converter (ADC) and stored in the computer memory.

Typically the pulse-acquire sequence is repeated many times and the digitised signals added together to improve the signal to noise ratio. The final data set is one of signal amplitude as a function of time. This data set may be Fourier transformed to convert it to signal amplitude as a function of frequency i.e. an NMR magnitude spectrum.

The strength of the $B_0$ shim field is then adjusted to typically change the static magnetic field by 0.1% to 0.5%. After this adjustment, the pulse sequence is performed again to produce a further data set which may also be Fourier transformed to convert it to a magnitude spectrum. In the further data set the resonant frequency of the nuclei of interest is changed in comparison to the first data set. However most spurious resonances from electrical or mechanical components of the apparatus, which are present in both data sets, have not changed in frequency between the two data sets.

The second data set (typically a magnitude spectrum) is subtracted from the first data set (typically a magnitude spectrum) by the software 14 to remove the spurious resonances from the resultant data set. Effectively, the procedure results in the filtering of the spurious resonances from the final spectrum and an increase in the signal-to-noise ratio. Further data sets obtained using different $B_0$ shim field strengths may be taken to perform more complex data manipulation, for example as discussed below in relation to FIGS. 4*a* to *c*.

At 0.256 T static magnetic field (low resolution in the terms discussed above), the intrinsic broadening effects are comparable with or greater than, the chemical shift magnitude of the different chemical groupings present in the sample so typically the resulting spectrum is simple, often a single peak, the area of the peak being proportional to the number of the nuclei of interest that are present.

Figure 4A:
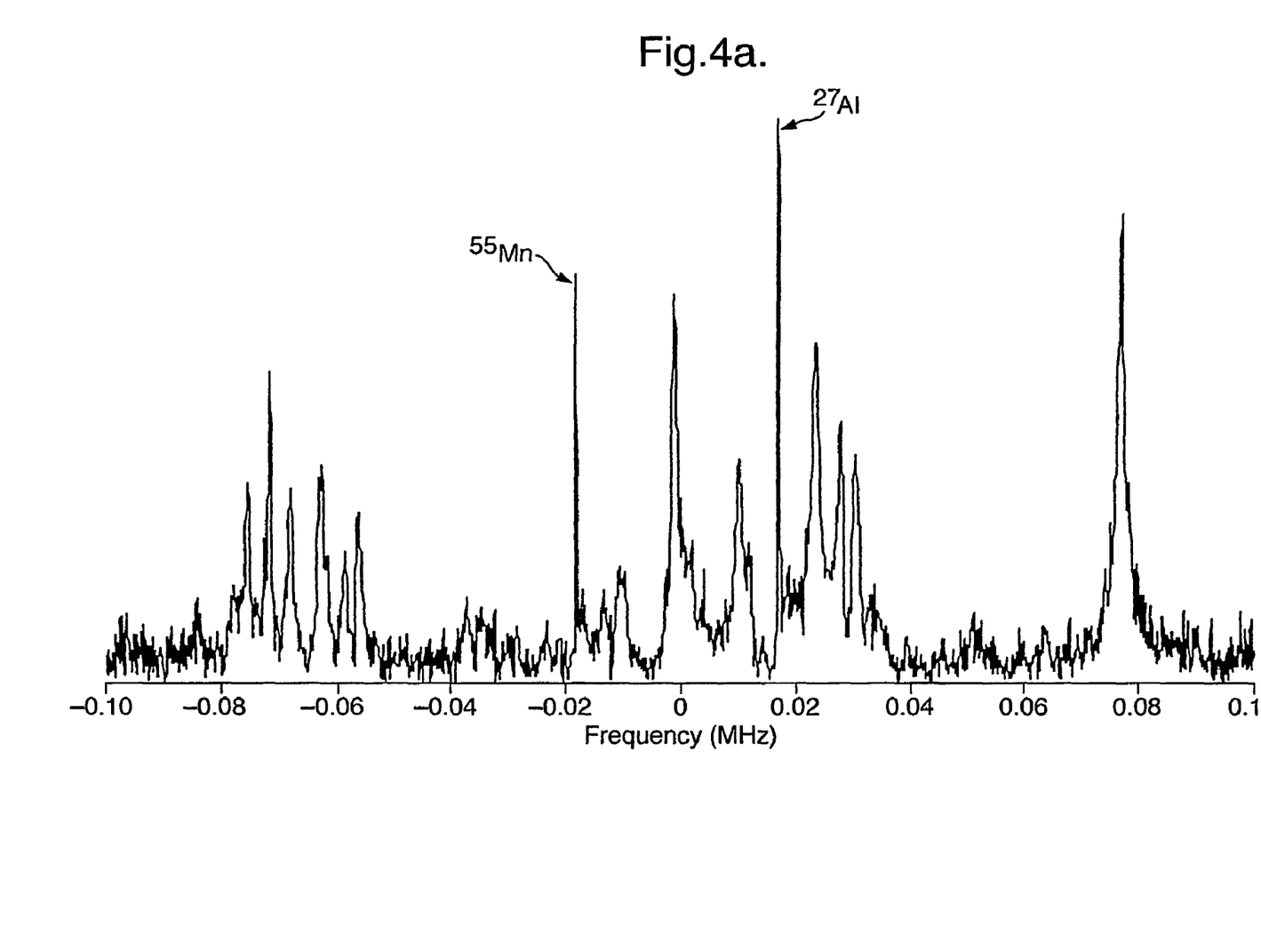
FIG. 4a shows the NMR spectrum obtained before filtering, the $^{55}$Mn and $^{27}$Al peaks are indicated.
Figure 4B:
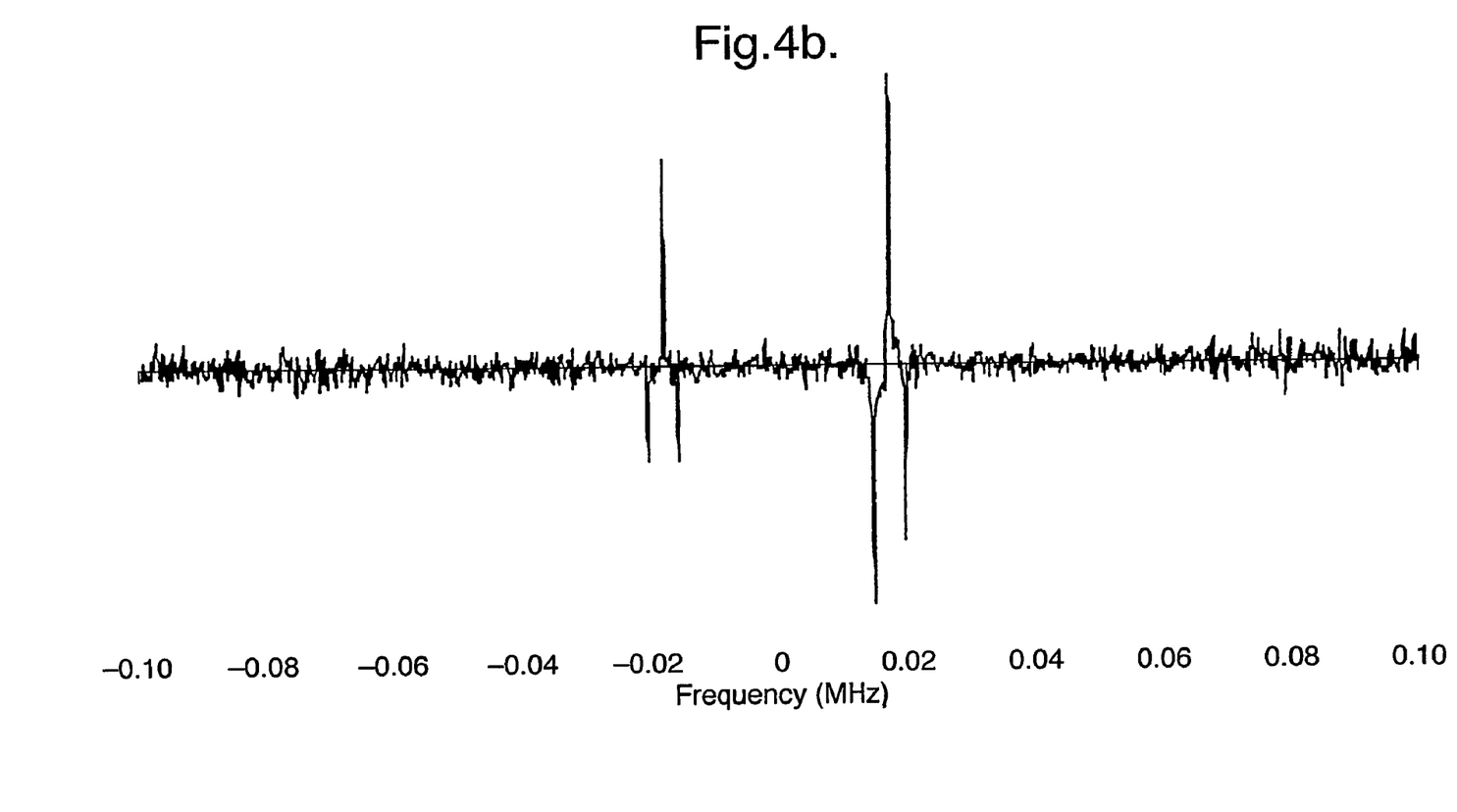
FIG. 4b shows the spectrum of FIG. 4a after filtering to remove spurious resonances.
Figure 4C:
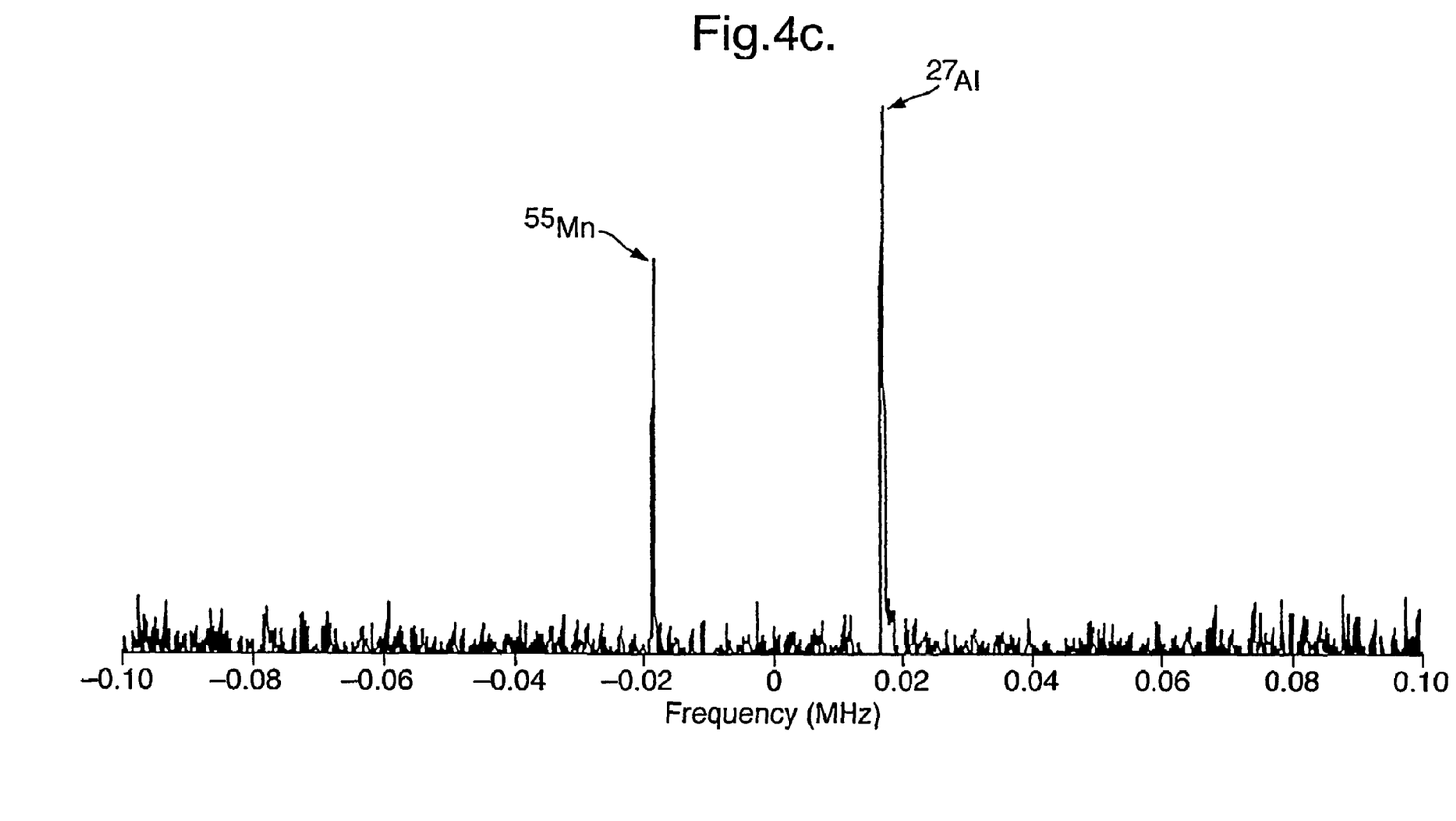
FIG. 4c shows the same filtered spectrum, but with all points below zero being eliminated.

An example of the results achieved using the NMR system in the manner described is shown in FIGS. 4*a*, *b* and *c*. In this example, three values of the $B_0$ shim field were used to produce a filtered spectrum by a simple data manipulation. The frequency of the coil in probe 6 was tuned and matched to the resonant frequency between that of $^{55}$Mn and $^{27}$Al, and a 1.0 molar solution of potassium permanganate in water and a 0.8 molar solution of aluminium nitrate in hydrochloric acid were placed in separate compartments within the sample chamber of the NMR apparatus. An NMR FID was taken, Fourier transformed and saved as the magnitude spectrum shown in FIG. 4a. $^{55}$Mn and $^{27}$Al peaks are visible, but the signal-to-noise ratio is low. The $B_0$ field strength was 0.256 T.

Using the $B_0$ shim coils, the $B_0$ field strength was first increased by 0.35% and then decreased by 0.35%. An NMR FID was taken at each new value of $B_0$, Fourier transformed and saved as a magnitude spectrum. A difference spectrum was generated between the magnitude spectra from the highest and middle values of the $B_0$ field and also between the lowest and middle. Spurious resonances were thereby filtered from each of these difference spectra. Finally the two difference spectra were subtracted to produce the spectrum of FIG. 4b which has a single positive peak for each of $^{55}$Mn and $^{27}$Al. The experiment shows that simultaneous identification of two different species at low field strengths is feasible.

FIG. 4c shows the same filtered spectrum as FIG. 4b, but eliminating all points below zero. The filtered spectrum has a significantly improved signal-to-noise ratio, measured not just by peak height but also by area-under-peak.

Other processing steps are possible, based on the same filtering principle of collecting different NMR data sets each obtained at a different $B_0$ shim field strength. These can be used to produce further data sets (for example spectra) appropriate to the type of application.

All software programmable control and data analysis is carried out using a PC computer interfaced with the spectrometer through conventional electronics. The software is provided by the manufacturer of the bench-top NMR system.

The invention claimed is:

1. A method for filtering spurious resonances from an NMR dataset, comprising the steps of:
   (a) creating a first, non-oscillating magnetic field of a predetermined field strength across a fluid sample,
   (b) intermittently exposing the sample to a second, oscillating magnetic field orthogonal to the first to generate an NMR signal,
   (c) detecting the NMR signal from the sample,
   (d) adjusting the first magnetic field to a different predetermined field strength and repeating steps (a) to (c), and
   (e) comparing the detected signals to obtain an NMR dataset from the sample from which spurious resonances, whose frequencies are unchanged by the adjustment to the first magnetic field, have been filtered,
   wherein the field strength of the first magnetic field is adjusted by 0.1% to 0.5%.

2. A method for filtering spurious resonances from an NMR dataset, comprising the steps of:
   (a) creating a first, non-oscillating magnetic field of a predetermined field strength across a fluid sample,
   (b) exposing the sample to a second, oscillating magnetic field orthogonal to the first,
   (c) continuously varying the field strength of the non-oscillating field and/or the frequency of the oscillating field to generate an NMR signal,
   (d) detecting the NMR signal from the sample,
   (e) adjusting the first magnetic field to a different predetermined field strength and repeating steps (a) to (d), and
   (f) comparing the detected signals to obtain an NMR dataset from the sample from which spurious resonances, whose frequencies are unchanged by the adjustment to the first magnetic field, have been filtered, wherein the field strength of the first magnetic field is adjusted by 0.1% to 0.5%.

3. A method according to claim 1, in which the filtered dataset is transformed into an NMR frequency domain spectrum.

4. A method according to claim 1, in which the detected signals are transformed into NMR frequency domain spectra before the comparison step.

5. A method according to claim 1, in which the field strength of the first magnetic field does not exceed 1.5 T.

6. A method according to claim 5, in which at least one of the generated NMR signals includes a fluid resonance, and the method further comprises the step of:
   analysing the filtered dataset to look for changes caused by a variation of the width and/or position of the fluid resonance in the NMR spectrum for the sample, the variation being indicative of the presence of an inhomogeneity in the fluid.

7. A method according to claim 5, in which for one or more of the generated NMR signals, the predetermined field strength of the non-oscillating field and/or the frequency of the oscillating field is selected in accordance with the magnetogyric ratio of an inhomogeneity or dissolved species to be detected in the fluid, and the method further comprises the step of:
   analysing the filtered dataset to look for changes in said one or more signals indicative of the presence of the inhomogeneity or dissolved species in the fluid.

8. A method according to claim 7, wherein two or more different atomic species are identifiable in the filtered dataset.

9. A method according to claim 1, in which a $B_0$ shim coil(s) is provided to adjust the first magnetic field to each different predetermined field strength.

10. A system for filtering spurious resonances from an NMR dataset comprising:
    a non-ferromagnetic, fluid sample holder;
    means for generating a first, non-oscillating magnetic field across the holder;
    means for adjusting the field strength of the first magnetic field by 0.1% to 0.5%;
    means for simultaneously generating a second, intermittent oscillating magnetic field across the holder;
    means for detecting resulting NMR signals from within the holder; and
    processing means operable in accordance with the method of claim 1 for comparing the detected signals to obtain an NMR dataset from the sample from which spurious resonances, whose frequencies are unchanged by the adjustment to the first magnetic field, have been filtered.

11. A system for filtering spurious resonances from an NMR dataset comprising:
    a non-magnetic, non-metallic, fluid sample holder;
    means for generating a first, non-oscillating magnetic field across the holder;
    means for adjusting the field strength of the first magnetic field by 0.1% to 0.5%;
    means for simultaneously generating a second, oscillating magnetic field across the holder;
    means for continuously varying the field strength of the non-oscillating field and/or the frequency of the oscillating field;
    means for detecting resulting NMR signals from within the holder; and
    processing means operable in accordance with the method of claim 2 for comparing the detected signals to obtain an NMR dataset from the sample from which spurious resonances, whose frequencies are unchanged by the adjustment to the first magnetic field, have been filtered.

12. A system according to claim 10, in which the means for adjusting the field strength of the first magnetic field is a $B_0$ shim coil(s).

13. A system according to claim 10, in which the field strength of the first magnetic field does not exceed 1.5 T.

14. A method according to claim 2, in which the filtered dataset is transformed into an NMR frequency domain spectrum.

15. A method according to claim 2, in which the detected signals are transformed into NMR frequency domain spectra before the comparison step.

16. A method according to claim 2, in which the field strength of the first magnetic field does not exceed 1.5 T.

17. A method according to claim 16, in which at least one of the generated NMR signals includes a fluid resonance, and the method further comprises the step of:

analysing the filtered dataset to look for changes caused by a variation of the width and/or position of the fluid resonance in the NMR spectrum for the sample, the variation being indicative of the presence of an inhomogeneity in the fluid.

18. A method according to claim 16, in which for one or more of the generated NMR signals, the predetermined field strength of the non-oscillating field and/or the frequency of the oscillating field is selected in accordance with the magnetogyric ratio of an inhomogeneity or dissolved species to be detected in the fluid, and the method further comprises the step of:

analysing the filtered dataset to look for changes in said one or more signals indicative of the presence of the inhomogeneity or dissolved species in the fluid.

19. A method according to claim 18, wherein two or more different atomic species are identifiable in the filtered dataset.

20. A method according to claim 2, in which a $B_0$ shim coil(s) is provided to adjust the first magnetic field to each different predetermined field strength.

21. A system according to claim 11, in which the means for adjusting the field strength of the first magnetic field is a $B_0$ shim coil(s).

22. A system according to claim 11, in which the field strength of the first magnetic field does not exceed 1.5 T.

* * * * *